United States Patent
Moy et al.

(10) Patent No.: US 8,760,660 B2
(45) Date of Patent: *Jun. 24, 2014

(54) PROCESS FOR PREDICTING AMOUNT OF COARSE FLAKES IN COATING COMPOSITIONS BY WET COLOR MEASUREMENT

(71) Applicant: Axalta Coating Systems IP Co., LLC, Wilmington, DE (US)

(72) Inventors: Anthony Moy, Garnet Valley, PA (US); Rajesh Gopalan Saliya, Philadelphia, PA (US); Ayumu Yokoyama, Wallingford, PA (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/666,481

(22) Filed: Nov. 1, 2012

(65) Prior Publication Data

US 2013/0107266 A1 May 2, 2013

Related U.S. Application Data

(60) Provisional application No. 61/554,044, filed on Nov. 1, 2011.

(51) Int. Cl.
  *G01N 21/55* (2014.01)
(52) U.S. Cl.
  USPC .......................................... 356/445; 356/448
(58) Field of Classification Search
  USPC ......... 362/153, 153.1, 249.03, 249.07, 249.1, 362/273, 287, 289, 523, 524, 528, 545, 362/249.02, 366, 421, 428; 356/445, 405, 356/71, 369, 370, 429, 448, 21, 36; 702/23; 250/221, 222.1, 559.04, 559.44; 359/589, 585, 586, 580
  See application file for complete search history.

(56) References Cited

U.S. PATENT DOCUMENTS

| | | | |
|---|---|---|---|
| 5,231,472 A | 7/1993 | Marcus et al. | |
| 6,583,878 B2 | 6/2003 | Hustert | |
| 7,990,536 B2 | 8/2011 | Lee et al. | |
| 2005/0056189 A1 | 3/2005 | Decker et al. | |
| 2013/0141727 A1* | 6/2013 | Yokoyama et al. ........... | 356/445 |

FOREIGN PATENT DOCUMENTS

| | | | |
|---|---|---|---|
| DE | 2525701 A1 | 12/1976 | |
| WO | 2004111587 A1 | 12/2004 | |
| WO | 2008103405 A1 | 8/2008 | |

OTHER PUBLICATIONS

ISA Korean Intellectual Property Office, International Search Report and Written Opinion for Application No. PCT/US2012/063094, dated Mar. 8, 2013.

* cited by examiner

*Primary Examiner* — Tri T Ton
(74) *Attorney, Agent, or Firm* — Ingrassia Fisher & Lorenz, P.C.

(57) ABSTRACT

A process for predicting an amount of coarse flakes, such as metallic aluminum flakes, present in a coating composition, such as automotive paint. The process includes measuring flop of a layer of the coating composition applied over a test substrate by using a flop prediction device. The process is repeated with varying amounts of one or more different types of coarse flakes added to the composition and the flop vs. amount of coarse flakes present in the coating composition is plotted on a graph. By using a curve fitting equation, a flake amount prediction curve then is obtained. By measuring the flop of a wet layer of a target coating composition, the amount of coarse flakes present in the target coating composition can be predicted by using the flake amount prediction curve.

13 Claims, 3 Drawing Sheets

# PROCESS FOR PREDICTING AMOUNT OF COARSE FLAKES IN COATING COMPOSITIONS BY WET COLOR MEASUREMENT

CROSS-REFERENCE TO RELATED APPLICATION

This application claims priority under 35 U.S.C. §119 from U.S. Provisional Application Ser. No. 61/554,044, filed Nov. 1, 2011, which is hereby incorporated by referenced in its entirety.

FIELD OF INVENTION

The present invention is directed to a process of predicting the amount of coarse flake distributed in a coating that results from a layer of a coating composition applied over a substrate, wherein said coating composition contains a combination of coarse and fine flakes. The process is more particularly directed to a quality assurance process that predicts on a real time basis the amount of coarse flakes distributed in a coating that would result from automotive OEM and refinish paints while such paints are being manufactured.

BACKGROUND OF INVENTION

Typically during the manufacturing of coating compositions, such as flake containing automotive OEM or refinish paints, from time to time, an aliquot of such coating compositions being manufactured is taken, applied as a layer of desired thickness over a test substrate, dried and/or cured into a coating and it's flop measured to check for the distribution of coarse flakes in the coating. The process parameters are then adjusted and the aforedescribed testing procedure is repeated until the adjusted coating composition meets the desired coarse flake distribution requirements.

The aforementioned testing procedure is not only time consuming and cumbersome but it also results in frequent interruptions in the manufacturing process. As a result, the batch-to-batch quality of the resulting coating compositions can be detrimentally affected. Therefore, a need exists to develop a process that could predict the distribution of coarse flakes in a coating that would result from a coating composition while it is still being manufactured such that the manufacturing process could be readily adjusted on a real time basis to get the desired flake distribution.

STATEMENT OF INVENTION

The present invention is directed to a process for predicting amount of coarse flakes in a target coating composition comprising:

(a) adding to a vessel of a flake prediction device a $S_0$ coating composition comprising $F_0$ parts by weight of said coarse flakes based on 100 parts by weight of said $S_0$ coating composition;

(b) dispensing from an opening in said vessel said $S_0$ coating composition over a test substrate to produce a $L_0$ layer of a substantially uniform thickness thereon;

(c) projecting on said $L_0$ layer a beam of light of a preset intensity at a preset angle of incidence from a light source;

(d) measuring $B_0$ flop of said beam reflected from said $L_0$ layer at a preset angle of reflectance by an optical measurement instrument;

(e) storing said $B_0$ flop of said $L_0$ layer in a computer usable storage medium of a computer;

(f) repeating said steps (a) through (f) for $S_1$ to $S_n$ coating compositions respectively comprising $F_1$ to $F_n$ parts by weight of said coarse flakes based on 100 parts by weight of said $S_1$ to $S_n$ coating compositions to determine $B_1$ to $B_n$ flops of $L_1$ to $L_n$ layers wherein n ranges from 1 to 100;

(g) locating intersecting points on a graph where said $B_0$ to $B_n$ flops of said $L_0$ to $L_n$ layers on X-axis of said graph intersect with said $F_0$ to $F_n$ parts by weight of said coarse flakes on Y-axis of said graph;

(h) using a curve fitting equation to produce a flake amount prediction curve on said graph;

(i) dispensing on said test substrate a $L_T$ layer of said substantially uniform thickness of said target coating composition from said vessel wherein said target coating composition contains said coarse flakes;

(j) projecting on said $L_T$ layer a beam of light at said preset intensity and at said preset angle of incidence from said light source;

(k) measuring $B_T$ flop of said beam reflected from said $L_T$ layer at said preset angle of reflectance by said optical measurement device;

(l) locating said $B_T$ flop of said $L_T$ layer on said X-axis of said graph;

(n) locating an intersecting point on said flake amount prediction curve that intersects with said $B_T$ flop on said X-axis of said graph; and (p) predicting amount of said coarse flakes contained in said target composition by locating $Y_T$ on said Y-axis of said graph that intersects with said intersecting point on said flake amount prediction curve that intersects with said $B_T$ on said X-axis of said graph.

DETAILED DESCRIPTION OF PREFERRED THE EMBODIMENT

Figure 1:
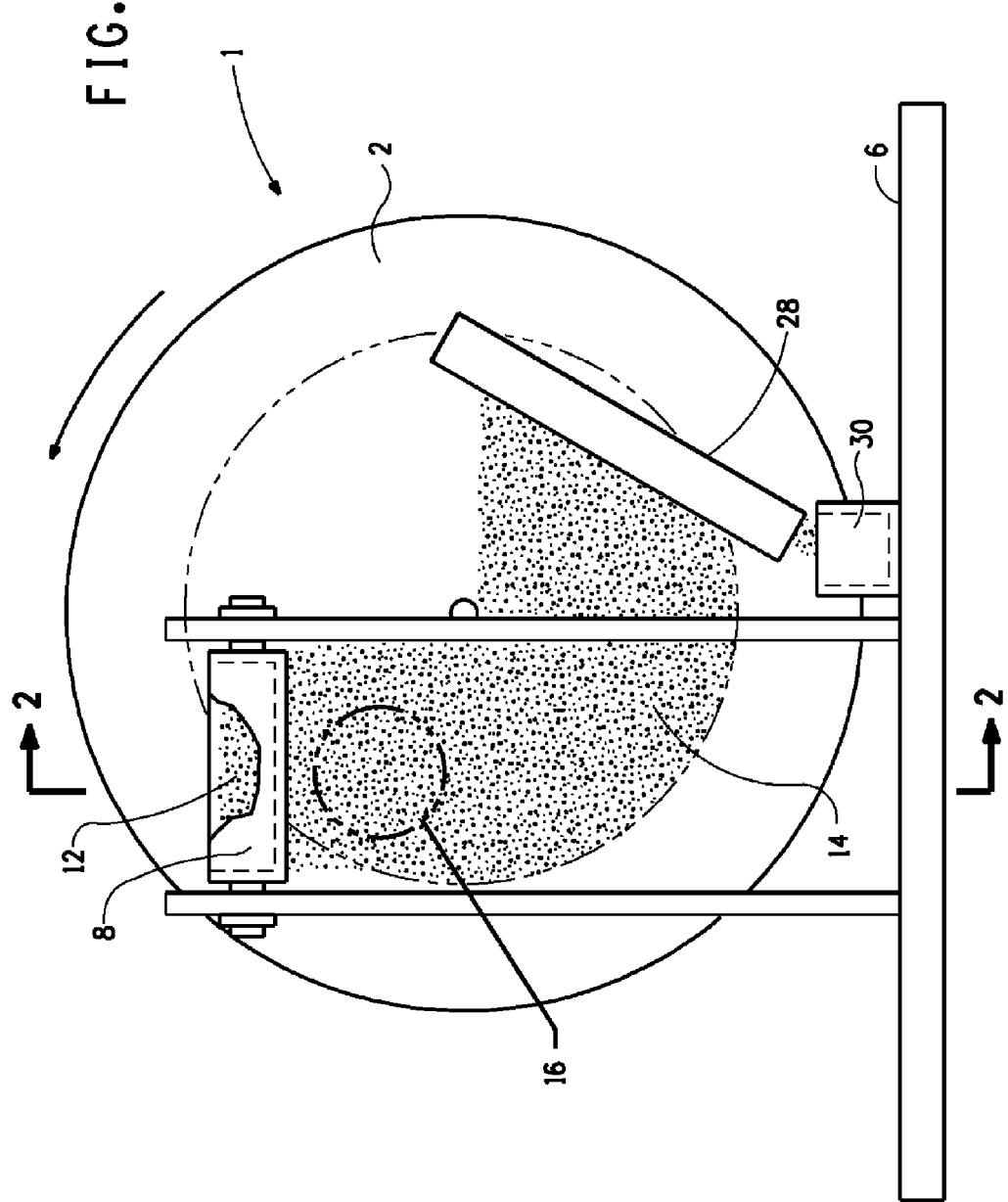
FIGS. 1 and 2 broadly illustrate one of the embodiments of a flake amount prediction device of the present invention.

As defined herein:

"Flakes" means conventional flakes used in coating composition that exhibit flop, such as conventional mica flakes, metallic flakes, such as Aluminum flakes, organic flakes or a combination thereof. Aluminum flakes are preferred.

"Coating composition" means a coating composition that contains a mixture of coarse and fine flakes that provide lustrous appearance, i.e., flop, to a coating composition applied over a substrate, such as an automotive body, bumper or a fender. By "flop" is meant the visual change in brightness or lightness of the flake, such as metallic aluminum flake, with a change in viewing angle, that is, a change from 90 degrees to 180 degrees. The greater the visual change from light to dark appearance, the better the flop. The flop accentuates the lines and curves of an automobile; therefore, it is very important in achieving this sought-after appearance of the coating. Automotive coating compositions containing metallic flakes, such as aluminum flakes are generally utilized to obtain the glossy lustrous appearance which is characteristically sought. The higher the amount of coarse flakes in the coating composition, the higher will be the flop of a coating resulting therefrom and vice versa. However, if one were to increase the amount of coarse flakes in the mixture of coarse and fine flake too much and reduce the amount of fine flakes in said mixture of coarse and fine flake too much, i.e., mostly coarse flakes and very little fine flakes, then coating properties of a coating resulting therefrom would be adversely affected, such as loss of hiding power of the coating, increased degree of cratering, increased degree orange peel, etc. The foregoing adverse effect on coating properties can be can be minimized by controlling the amount of coarse flakes in the mixture of coarse and fine flake in the metallic coating compositions. The size of the coarse flakes included in the flake mixture of coating compositions can range from 25 microns to 2000 microns, preferably from 25 microns to 500 microns, and more preferably 25 to 100 microns. The size of the fine flakes included in the flake mixture of coating compositions can range from 1 micron to 20 microns and preferably from 5 microns to 20 microns. In a typical coating composition process various components, of a coating composition, such as pigments, flakes, binder polymers, solvents, etc, are mixed and sometimes ground in ball mills. As a result of such grinding or mixing processes, the size of the coarser flakes can be reduced. Therefore, it becomes difficult to predict the amount of coarse flakes that still exist at the end of such a manufacturing process. Therefore, by ascertaining the amount of coarse flakes present in the coating composition while it is being made, process parameters can be adjusted in real time during the manufacture to finally attain coating compositions that contain a desired amount of the coarse flakes.

A flop of a layer from a coating composition in its wet state when measured directly can correlate to the flop that can result when such a layer dries and/or cures into a coating. However, since the optically proprieties of a wet layer of a coating composition continuously changes due to evaporation of solvent from and/or crosslinking of the wet layer, it is very difficult to correlate such wet optical property measurements to the flop of a coating that results from such a layer once it dries and/or cures into a coating. The process and the device of the present invention provide a solution to attaining the aforedescribed correlation.

Figure 2:
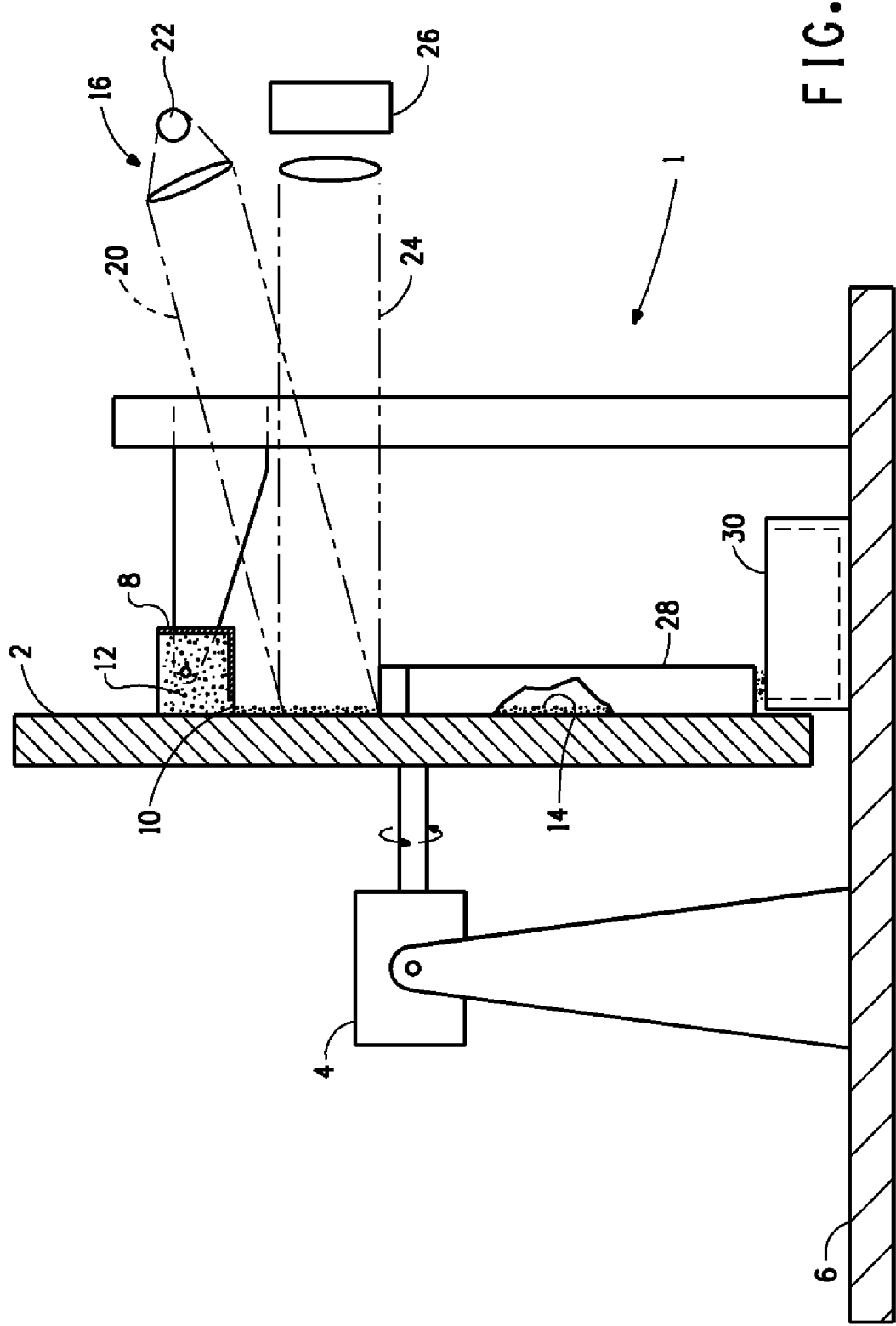

One of the flop prediction devices suitable for the process of the present invention includes a device 1 shown in FIGS. 1 and 2. Device 1 includes a test substrate 2, preferably a disc, rotated by a driver 4, such as an electric motor, which is positioned on a support frame 6. Test substrate 2 mounted on a shaft of driver 4 can be positioned either in a horizontal or in a vertical position. Test substrate 2 of device 2 shown in FIGS. 1 and 2 is positioned vertically, which is preferred. Test substrate 2 can be made of any suitable material, such as steel, plastic or aluminum. The surface of test substrate 2 preferably has the same degree of smoothness as that of, for example, auto body or auto bumper such that the results obtained are as close to those that would have been obtained under similar paint application conditions.

As shown in FIG. 1, Device 1 is provided with a vessel 8 positioned adjacent to test substrate 2. Vessel 8 is provided with an opening 10, preferably a slot, through which a coating composition ($S_0$) 12, when poured into vessel 8, can be applied as a $L_0$ layer 14 of a substantially uniform thickness on a measurement area 16 on the surface of test substrate 2. Coating composition ($S_0$) 12 used in producing $L_0$ layer 14 contains $F_0$ parts by weight of coarse flakes based on 100 parts by weight of coating composition ($S_0$) 12. As test substrate 2 is rotated by driver 4, preferably for about a quarter turn, $L_0$ layer 14 is created. Opening 10 is adjacent to substrate 2 such that a resulting gap between opening 10 and substrate 2 controls the thickness of $L_0$ layer. Typically, $L_0$ layer is provided with a thickness that ranges from 6 micrometers to 2300 micrometers.

Flop prediction device 1 of the present invention includes a conventional optical measurement mechanism 16 provided with conventional collimators for producing a beam of light 20 of preset intensity at a preset angle that can be projected on measurement area 16 from a conventional light source 22. A $B_0$ flop 24 of beam of light 20 off of $L_0$ layer 14 can then be measured by a conventional optical measurement instrument 26, such as MA-68 flop measurement device supplied by X-Rite of Grand rapids, Mich. Any angle of incidence and reflectance can be used. However, a 60 degree angle of reflectance is typically employed and reflectance is preferably measured before there is substantial change in the optical characteristics of $L_0$ layer 14, which depend on the physical and chemical properties of the coating composition from which $L_0$ layer 14 is produced. Thus, the higher the content of the solvent in the coating composition, the longer would be the window during which the flop can be measured and vice versa. Coating compositions that are lacquers (those containing high molecular weight non-reactive binder polymers dissolved in a solvent) typically would have longer measurement window than coating compositions that are enamels (those containing binder polymers containing reactive groups that chemically react with crosslinking groups on crosslinking agents that are mixed before being applied as a layer on a substrate). Typically, the flop is measured within 2 seconds to two minutes after $L_0$ layer 14 is applied over test substrate 2.

Means for configuring computer readable program code devices is used to cause a conventional computer to store $B_0$ flop 24 of $L_0$ layer 14 in a computer usable storage medium of the computer (not-shown in FIG. 1). The computer is preferably in communication with optical measurement instrument 26. If desired, the computer can be in communication with a remote computer, such as an offsite computer used to gather information from one or more computers connected to flop prediction devices of the present invention.

If desired, after $B_0$ flop of $L_0$ layer is measured, substrate 2 can be rotated further by driver 4 to scrape off the coating with a doctor blade 28 into a waste container 30 and substrate 2 can then be cleaned. Alternatively, after $B_0$ flop is measured, substrate 2 can be removed; $L_0$ layer scraped off of substrate 2 and then substrate 2 is cleaned for the next step.

The aforedescribed procedure is then repeated with series of $S_1, S_2, \ldots S_n$ (n being in the range of 1 to 100, preferably from 2 to 50 and more preferably from 5 to 20) coating compositions 12 containing increasing amounts of one or more coarse flakes ranging from $F_1$ to $F_n$ weight parts per 100 weight parts of coating composition. The increasing amount of flakes added to the coating composition can be preferably increased in suitable set amounts, such as 0.001, 0.01, 0.1, 0.5, 1, 5, 10, 15 weight parts in per 100 weight parts of the coating composition, with $F_0$ ranging from 0.001 weight part to 5 weight parts per 100 weight parts of the coating composition and $F_n$ ranging from 5.1 weight parts to 60 weight parts per 100 weight parts of coating composition. The ratio of coarse flakes to fine flakes in the flake combination can range from 98/2 to 50/50. As described above, $B_1$ flop 24 from a $L_1$ layer 14 from $S_1$ coating composition is measured and the means for configuring computer readable program code devices is used to cause the computer to store $B_1$ flop 24 of $L_1$ layer 14 in the computer usable storage medium of the computer. The process is repeated till $B_n$ flop from a $L_n$ layer 14 from coating composition $12_n$ is measured and stored in the computer usable storage medium of the computer.

The means for configuring computer readable program code devices is used to cause the computer to locate intersecting points on a graph where $B_0$ to $B_n$ flops of $L_0$ to $L_n$ layers 14 on X-axis of the graph intersect with the $F_0$ to $F_n$ parts by weight of coarse flakes, respectively based on $S_0$ to $S_n$ coating compositions, on Y-axis of the graph. The means for configuring computer readable program code devices is then used to cause the computer to use a curve fitting equation to produce a flake amount prediction curve on the graph. Preferably, the curve fitting equation is a second degree polynomial equation. More preferred second degree polynomial equation is of the following formula:

$$\text{Flop } Y = a(B_n)^2 + b(B_n) + c \quad (1)$$

$$R^2 = Z \quad (2)$$

wherein said constants a, b, c and $R^2$ are determined by a curve fitting process, such as that described in Microsoft Office Excel® 2003 supplied by Microsoft Corporation of Redmond, Wash. Z is a statistical measure of how close the curve fits to the experimental datum points on a graph. When Z is equal to 1, it is considered to be an ideal fit, i.e., all the experimental datum points lay on the fit curve. All the necessary and relevant information is stored on the computer usable storage medium.

If desired, the flop amount prediction curve on the graph may be displayed on a conventional monitor and/or printed on paper by means of a conventional printer both of which being in communication with the computer.

Once the flop amount prediction curve on the graph is produced, the user can use the flop prediction device of the present invention to predict the flop of a target coating composition containing an unknown or known amount of one or more flakes without going through the cumbersome and time consuming process of curing the layer into a coating. $L_T$ layer 14 (also know as target layer) from the target coating composition, preferably having the same substantially uniform thickness as the layers used in creating the flop amount prediction curve, dispensed over substrate 2 of flop amount prediction device 1 of the present invention can be used in a production set up that allows the manufacturer of a coating composition to expeditiously adjust the ingredients of the coating composition for ensuring that the resulting coating composition has a desired flop.

As described above, $B_T$ reflectance 24 from $L_T$ layer 14 from the target coating composition is measured and the means for configuring computer readable program code devices is used to cause the computer to store $B_T$ flop 24 of $L_T$ layer 14 in the computer usable storage medium of the computer.

The means for configuring computer readable program code devices is used to cause the computer to locate $B_T$ flop of $L_T$ layer on the X-axis of the graph. The means for configuring computer readable program code devices is used to cause the computer to locate an intersecting point on the flake amount prediction curve that intersects with $B_T$ on X-axis of the graph. Finally, The means for configuring computer readable program code devices is used to cause the computer to predict the flop of a target coating resulting from $L_T$ layer by locating $Y_T$ flop on the Y-axis of the graph that intersects with the intersecting point on the flake amount prediction curve that intersects with $B_T$ on the X-axis of the graph.

As a result, once the flake amount prediction curve is stored in a computer of device 1, an aliquot of a coating composition being made can be applied as a layer and its flop measured to predict the amount of the coarse flake in said composition. If the amount measured falls outside of desired specification, the manufacturing process can be adjusted without interruption by monitoring the amount of coarse flake on a continuing basis.

Few of the aspects of the aforedescribed flop prediction device 1 of the present invention are described in German patent application DT 25 25 701 A1. It should be understood that substrate 2 need not be positioned vertically or have to have a disc shape. Other embodiments, such as those where substrate is positioned horizontally, or is in the form of a belt, etc. are also well suited for the process of the present invention. For example, substrate in the form of a roller, as described in a commonly assigned U.S. Pat. No. 6,583,878 to Hustert, is also well suited for the process of the present invention.

One embodiment of the process of the present invention utilizes flop prediction device 1 of FIG. 1. The process includes dispensing on substrate 2, $L_0$ layer 14 of a substantially uniform thickness of coating composition 12 through vessel 8, which contains coating composition 12. Then beam of light 20 of a preset intensity at a preset angle of incidence from light source 22 is projected on measurement area 16 of $L_0$ layer. By means of optical measurement instrument 26, $B_0$ flop of beam of light 20 is measured at a preset angle of reflectance. $B_0$ flop of $L_0$ layer is then stored in the computer usable storage medium of the computer. The aforedescribed steps are repeated for $S_1$ to $S_n$ coating compositions 12 further comprising $F_1$ to $F_n$ parts by weight of one or more flakes based on 100 parts by weight of the coating composition respectively to determine $B_1$ to $B_n$ flops of $L_1$ to $L_n$ layers wherein n ranges from 1 to 100.

EXAMPLES

Table 1 below lists coating composition samples which include varied mixtures of coarse flakes (Sparkle Silver 3641 flakes having an average size of 31 microns, which were supplied by Silberline of Tamaqua, Pa.) and fine flakes (Aluminum paste 33313 flakes having an average size of 15 microns, which was supplied by Eckart of Louisville, Ky.) mixed with 780™ polymer supplied by DuPont Company of Wilmington. Layers of these samples were applied over substrate 2 of Device 1 and flops of the layers were measured using MA-68 color instrument 26 supplied by X-Rite of Grand Rapids, Mich.:

TABLE 1

|  | Sample 1 | Sample 2 | Sample 3 | Sample 4 | Sample 5 |
| --- | --- | --- | --- | --- | --- |
| Weight in grams of fine Flakes | 100 | 80 | 60 | 30 | 0 |
| Weight in grams of coarse Flakes | 0 | 20 | 40 | 70 | 100 |
| Weight of Polymer | 900 | 900 | 900 | 900 | 900 |
| Total weight | 1000 | 1000 | 1000 | 1000 | 1000 |
| Flop of liquid layer | 12.8 | 13.1 | 13.5 | 14.3 | 15.8 |

Figure 3:
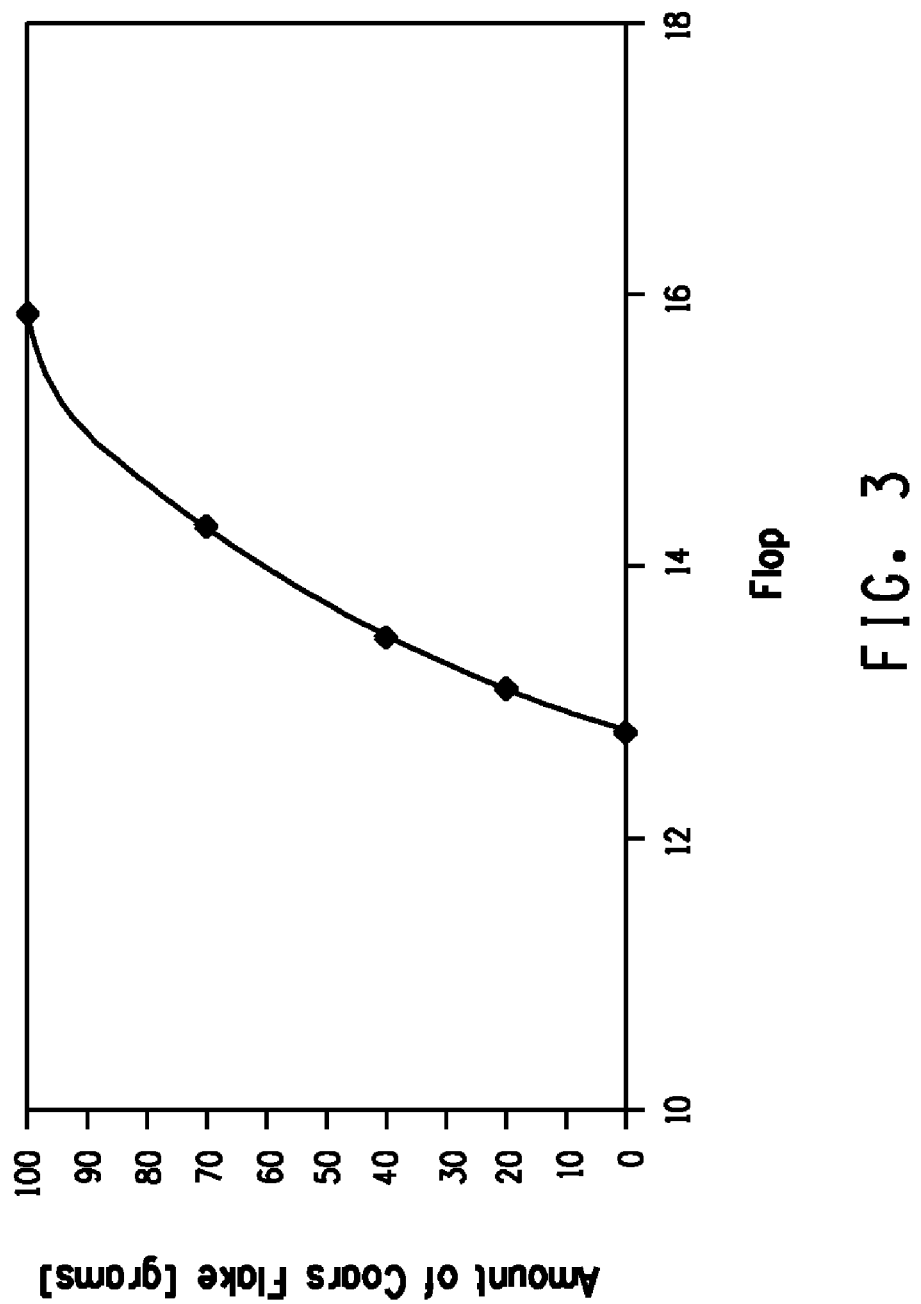
FIG. 3 broadly illustrates the flake amount prediction curve produced by the flake amount prediction process of the present invention.

As shown in FIG. 3, intersecting points on a graph where $B_0$ to $B_n$ of $L_0$ to $L_n$ layers on X-axis of the graph intersect with $F_0$ to $F_n$ amounts of coarse flakes of $S_0$ to $S_n$ coating compositions on Y-axis of the graph are then located.

Using a curve fitting equation, such as the aforementioned secondary degree polynomial equation (1) is then used to produce a flop amount prediction curve, such as that shown in FIG. 3. The term "a" in the equation (1) was 9.1513. The term "b" in the equation (1) was 294.53 and the term "c" in the equation was 2269.2. The statistical measure Z was 0.999. All of the foregoing terms were obtained by using the aforementioned Microsoft Excel® program. It would be readily to apparent to one of ordinary skill in the art that the statistical measure Z of 0.999 indicates the curve of the flop amount prediction was a very close fit to the Z of an ideal fit being 1.

The process of the present invention is then used to predict the flop of a target coating composition by first dispensing on substrate 2 a $L_T$ layer of preferably the same substantially uniform thickness of a target coating composition through vessel 8 of flop amount prediction device 1 containing the target coating composition further comprising an unknown or a known amount of the coarse flakes. A beam of light 20 at the preset intensity and at the preset angle of incidence from light source 22 is then projected on measurement area 16 of $L_T$ layer and $B_T$ flop of beam reflected from $L_T$ layer at the preset angle of reflectance is measured by optical measurement instrument 26. An intersecting point on the flop amount prediction curve that intersects with $B_T$ flop on the X-axis of said graph is then located and flake amount at the preset flop angle of a coating resulting from $L_T$ layer is then predicted by locating $Y_T$ on the Y-axis of the graph.

Thus, one of ordinary skill in the art can readily see that the amount of coarse flakes can be readily predicted by the flop amount prediction curve of the process of the present invention by just measuring the flop of a wet layer of a coating composition.

The process and device of the present invention is most suitable for predicting the flop of automotive OEM and refinish paints during their manufacture.

What is claimed is:

1. A process for predicting amount of coarse flakes in a target coating composition comprising:
    (a) adding to a vessel of a flake prediction device a $S_0$ coating composition comprising $F_0$ parts by weight of said coarse flakes based on 100 parts by weight of said $S_0$ coating composition;
    (b) dispensing from an opening in said vessel said $S_0$ coating composition over a test substrate to produce a $L_0$ layer of a substantially uniform thickness thereon;
    (c) projecting on said $L_0$ layer a beam of light of a preset intensity at a preset angle of incidence from a light source;
    (d) measuring $B_0$ flop of said beam reflected from said $L_0$ layer at a preset angle of reflectance by an optical measurement instrument;
    (e) storing said $B_0$ flop of said $L_0$ layer in a computer usable storage medium of a computer;
    (f) repeating said steps (a) through (f) for $S_1$ to $S_n$ coating compositions respectively comprising $F_1$ to $F_n$ parts by weight of said coarse flakes based on 100 parts by weight of said $S_1$ to $S_n$ coating compositions to determine $B_1$ to $B_n$ flops of $L_1$ to $L_n$ layers wherein n ranges from 1 to 100;
    (g) locating intersecting points on a graph where said $B_0$ to $B_n$ flops of said $L_0$ to $L_n$ layers on X-axis of said graph intersect with said $F_0$ to $F_n$ parts by weight of said coarse flakes on Y-axis of said graph;
    (h) using a curve fitting equation to produce a flake amount prediction curve on said graph;
    (i) dispensing on said test substrate a $L_T$ layer of said substantially uniform thickness of said target coating composition from said vessel wherein said target coating composition contains said coarse flakes;
    (j) projecting on said $L_T$ layer a beam of light at said preset intensity and at said preset angle of incidence from said light source;
    (k) measuring $B_T$ flop of said beam reflected from said $L_T$ layer at said preset angle of reflectance by said optical measurement device;
    (l) locating said $B_T$ flop of said $L_T$ layer on said X-axis of said graph;
    (n) locating an intersecting point on said flake amount prediction curve that intersects with said $B_T$ flop on said X-axis of said graph; and
    (p) predicting amount of said coarse flakes contained in said target composition by locating $Y_T$ on said Y-axis of said graph that intersects with said intersecting point on said flake amount prediction curve that intersects with said $B_T$ on said X-axis of said graph.

2. The process of claim 1 wherein said optical measurement device is a spectrophotometer.

3. The process of claim 1 wherein said optical measurement instrument is in communication with said computer.

4. The process of claim 1 wherein said coarse flakes having a size ranging from 25 microns to 2000 microns.

5. The process of claim 1 wherein said opening is a slot adjacent to said test substrate such that a resulting gap between said slot and said test substrate controls the thickness of said $L_0$ to $L_n$ layers.

6. The process of claim 1 wherein said $L_0$ to $L_n$ layers are of the same thickness ranging from 6 micrometers to 2300 micrometers.

7. The process of claim 1 wherein said test substrate is a disc positioned substantially vertically on a support frame of said flake prediction device.

8. The process of claim 1 wherein said curve fitting equation is a second degree polynomial equation.

9. The process of claim 8 wherein said second degree polynomial equation is of the formula:

$$\text{Flop } Y = a(B_n)^2 + b(B_n) + c$$

$$R^2 = Z$$

wherein said constants a, b, c and Z are determined by a curve fitting process.

10. The process of claim 1 comprising displaying said predicted amount of said coarse flakes contained in said target coating composition on a CRT monitor.

11. The process of claim 1 comprising communicating said predicted amount of said coarse flakes contained in said target coating composition from said computer to a remote computer.

12. The process of claim 1 wherein said target coating composition is an automotive OEM or refinish paint.

13. The process of claim 1 wherein said coarse flakes are aluminum flakes, mica flakes, inorganic flakes, organic flakes or a combination thereof.

* * * * *